United States Patent [19]
Brion et al.

[11] Patent Number: 5,391,569
[45] Date of Patent: Feb. 21, 1995

[54] NEW CHROMENE COMPOUNDS HAVING A TRIENE SIDE CHAIN

[75] Inventors: Jean-Daniel Brion, Saint-Leu-La-Foret; Guillaume Le Baut, Saint-Sebastien-sur-Loire; Guillaume Poissonnet, Villebon S/Yvette; Lucy De Montarby, Courbevoie; Larbi Belachmi, Nantes; Jacqueline Bonnet, Paris; Massimo Sabatini, Garges; Charles Tordjman, Boulogne, all of France

[73] Assignee: Adir et Compagnie, Courbevoie, France

[21] Appl. No.: 127,804

[22] Filed: Sep. 28, 1993

[30] Foreign Application Priority Data

Sep. 29, 1992 [FR] France ................... 92 11592
Sep. 29, 1992 [FR] France ................... 92 11591

[51] Int. Cl.⁶ ............ A61K 31/35; A61K 31/47; A61K 31/445; A61K 31/40
[52] U.S. Cl. .................. 514/456; 514/311; 514/314; 514/320; 514/422; 546/152; 546/167; 546/196; 546/269; 548/454; 548/525; 549/407; 549/408
[58] Field of Search .......... 549/407, 408; 514/456, 514/311, 314, 320, 422; 546/152, 167, 196, 269; 548/454, 525

[56] References Cited

U.S. PATENT DOCUMENTS

| | | | |
|---|---|---|---|
| 4,544,758 | 10/1985 | Vogel et al. | 549/408 |
| 4,879,284 | 11/1989 | Laup et al. | 549/408 |
| 4,975,454 | 12/1990 | Brion et al. | 514/456 |
| 5,045,551 | 9/1991 | Chandraratra | 549/407 |
| 5,260,294 | 11/1993 | Walser | 549/408 |

OTHER PUBLICATIONS

Brion et al. Chem. Abst. 113:58938e (1990) (EP-337885, Oct. 1989).

*Primary Examiner*—Cecilia Tsang
*Attorney, Agent, or Firm*—Gordon W. Hueschen

[57] ABSTRACT

A compound selected from those of formula (I):

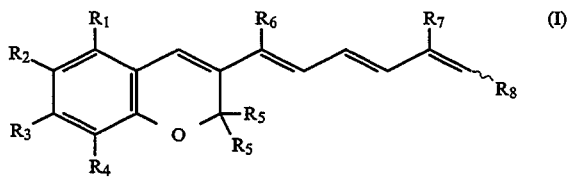

in which the groups $R_1$ to $R_8$ are as defined the description.

Medicaments.

20 Claims, No Drawings

NEW CHROMENE COMPOUNDS HAVING A TRIENE SIDE CHAIN

The present invention relates to new chromene compounds a triene side chain, to a process for the preparation thereof, to pharmaceutical compositions containing them, and to their use in the treatment of osteoporosis and inflammatory disorders.

It is known that osteoporosis can be treated by inhibiting bone resorption or by promoting the formation of bone tissue.

The compounds used in the treatment of osteoporosis are either anti-resorption agents, such as calcitonin and its derivatives, or agents that generate bone tissue, such as fluorine salts.

The compounds of the invention possess a novel structure comprising a triene chain attached to an optionally substituted bicyclic structure of the chromene type. These compounds have a superior pharmacological value as compared with the reference compounds by virtue of the fact that they act both as anti-bone resorption agents and as regenerators of bone tissue, that activity being exhibited more rapidly and at a lower dose.

Moreover, the compounds of the invention have the ability to inhibit phospholipase $A_2$, which is involved in all inflammation processes. It is known that the inflammatory process may induce resorption at bone level, osteopoenia.

These three properties show that the compounds of the invention present a complete and unique method of treating the principal bone diseases on account of their anti-bone resorption ability, their ability to generate osteoid tissue and their anti-osteopoenic ability.

More precisely, the present invention relates to compounds of the general formula (I):

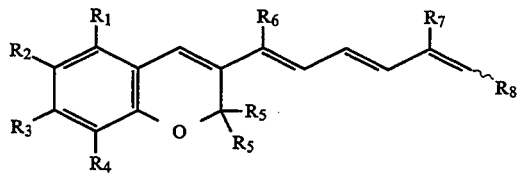

in which:
$R_1$, $R_2$, $R_3$ and $R_4$, which are the same or different, are selected from:
hydrogen,
halogen,
substituted or unsubstituted phenyl,
adamantyl,
substituted or unsubstituted heterocyclic containing 5 or 6 atoms, selected from furyl, pyrrolyl, pyrrolidinyl, thienyl, pyridyl, piperidyl, indolyl and quinolyl,
R', and
OR',
R' being linear or branched alkyl containing 1 to 6 carbon atoms inclusive that is optionally substituted by one or more hydroxy and/or by one or more halogens,
$R_5$, $R_6$ and $R_7$, which are the same or different, are selected from hydrogen and linear or branched alkyl containing 1 to 6 carbon atoms inclusive,
$R_8$ is selected from $C(O)OR_9$, $P(O)(OR_9)_2$ and $CONHR_{10}$ in which $R_9$ is hydrogen, linear or branched alkyl containing 1 to 6 carbon atoms inclusive, or a residue of an amino-sugar, for example glucuronide, and $R_{10}$ represents hydrogen, linear or branched alkyl containing 1 to 6 carbon atoms inclusive, or optionally substituted aryl,
the non-defined bond carrying $R_8$ being a single bond conferring an E- or Z-configuration on the double bond supporting it,
with the proviso that when $R_5$ represents hydrogen and $R_6$ and $R_7$ each represents methyl and $R_8$ represents $C(O)OR_9$ as defined above, then at least one of the substituents $R_1$, $R_2$, $R_3$ and $R_4$ is other than hydrogen, halogen, R' and OR', R' being as defined above,
their stereoisomers and, where appropriate, their addition salts with a pharmaceutically-acceptable acid or base.

The present invention relates also to a process for the preparation of the compounds of formula (I), characterised in that the compound of formula (II):

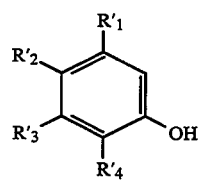

in which $R'_1$, $R'_2$, $R'_3$ and $R'_4$, which are the same or different, represent hydrogen, halogen, or linear or branched alkyl or alkoxy containing 1 to 6 carbon atoms inclusive that is optionally substituted by one or more OH and/or by one or more halogen, is converted into the compound of formula (III):

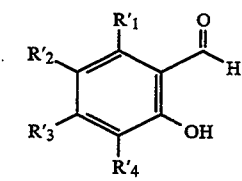

in which $R'_1$, $R'_2$, $R'_3$ and $R'_4$ have the same meanings as above,
by the Sommelet reaction, by the action of paraformaldehyde in the presence of hexamethylenetetramine, at a temperature of 100° C., followed by acidification,
or alternatively by the action of a metal chloride, for example tin tetrachloride, in the presence of an alkylamine, such as trioctylamine, with trioxymethylene, likewise at 100° C.,
which compound of formula (III) is then cyclised by the action of a compound of formula (IV):

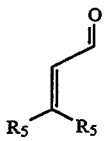

in which $R_5$ is as defined in formula (I),
in the presence of an alkali metal carbonate, such as potassium carbonate, in a polar solvent at reflux, such as dioxane or butan-2-one, to give the compound of formula (V):

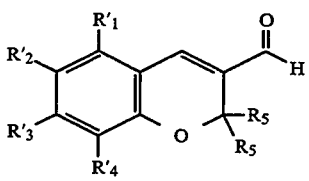
(V)

in which $R'_1$, $R'_2$, $R'_3$, $R'_4$ and $R_5$ are as defined above, it being possible for the groups $R'_1$, $R'_2$, $R'_3$ and $R'_4$ of that compound of formula (V), when one or more of those groups represents a halogen, to be replaced by phenyl, substituted phenyl, adamantyl, or by a heterocyclic radical as defined above, by reaction with a corresponding tetra-phenyl-, -aryl-, -heterocyclyl- or -heteroaryl-tin, in the presence of a palladium-based catalyst, such as, for example, transbenzyl(chloro)-bis(triphenylphosphine)palladium(II) in toluene at reflux, thereby obtaining all the various compounds of formula (VI):

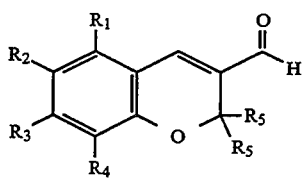
(VI)

in which $R_1$, $R_2$, $R_3$, $R_4$ and $R_5$ have the same meanings as above, which, by means of a Wittig reaction with the aid of a compound of formula (VII):

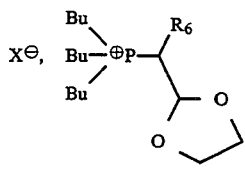
(VII)

in which X is halogen and $R_6$ is as defined above,
in a solvent such as dimethylformamide, followed by acid hydrolysis, give the compound of formula (VIII):

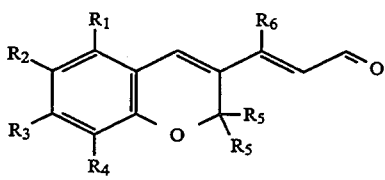
(VIII)

in which $R_1$, $R_2$, $R_3$, $R_4$, $R_5$ and $R_6$ are as defined above,
which compound of formula (VIII), after a second Wittig reaction, under the same conditions, with a compound of formula (VII'):

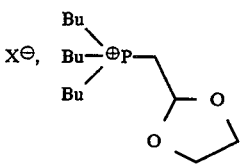
(VII')

in which X is as defined above,
is converted into the compound of formula (IX):

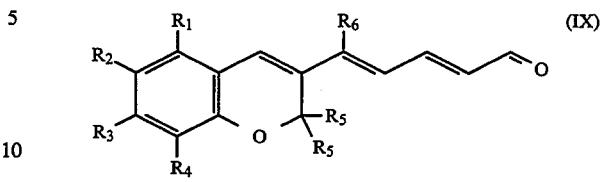
(IX)

in which the groups $R_1$ to $R_6$ are as defined above,
which, finally, is treated with a compound of formula (Xa) or (Xb):

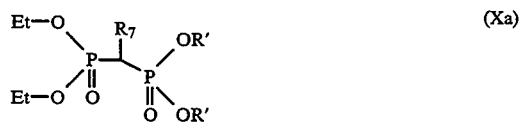
(Xa)

(Xb)

in which $R_7$ and $R'$ are as defined above,
to give the compounds of formulae (Ia) and (Ib), respectively:

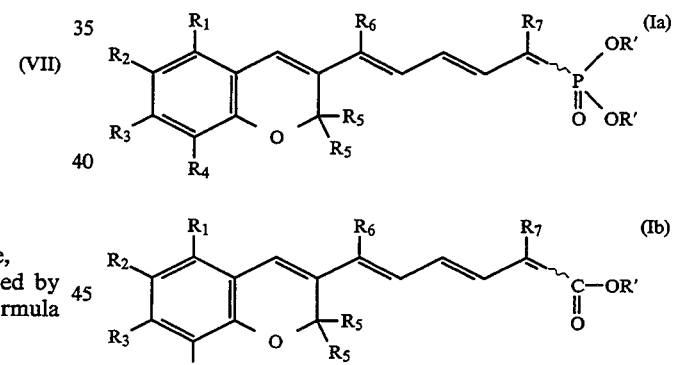
(Ia)

(Ib)

in which the groups $R_1$ to $R_7$ and $R'$ are as defined above,
which compound of formula (Ia) may be treated in a basic or acidic medium to obtain the compound of formula (Ic):

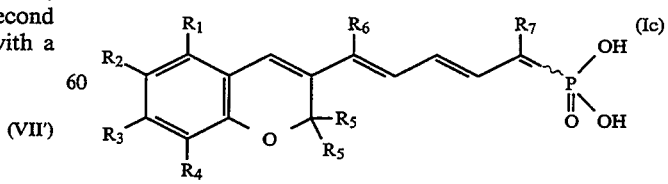
(Ic)

in which the groups $R_1$ to $R_7$ are as defined above,
which compound of formula (Ib) may be hydrolysed to form the compound of formula (Id):

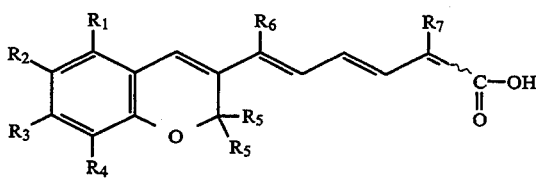

in which the groups $R_1$ to $R_7$ are as defined above, which, in turn, after conversion into its corresponding acyl chloride and treatment with an amine of formula (XI):

$$R_{10}-NH_2 \quad (XI)$$

in which $R_{10}$ is as defined above,
yields the compound of formula (Ie):

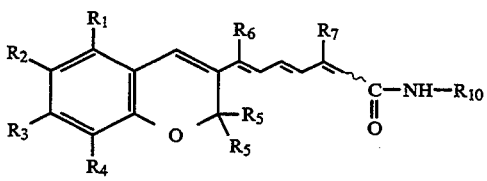

in which the groups $R_1$ to $R_7$ and $R_{10}$ are as defined above, all the various compounds of formulae (Ia) to (Ie) forming the compounds of the general formula (I) in their entirety, which compounds are purified, where appropriate, by a conventional purification method, and the stereoisomers of which are separated, if desired, by a conventional separation method, and which are converted, if necessary, into their addition salts with a pharmaceutically-acceptable acid or base.

The new compounds of the present invention have valuable pharmacological and therapeutic properties. In particular, these compounds have been shown to possess anti-osteoporotic properties, an ability to form bone tissue, and an anti-inflammatory activity in general.

In general, the compounds of the present invention are used in the preventive or non-preventive treatment of osteoporosis on account of their anti-resorption property, their ability to form bone tissue and their anti-inflammatory action, allowing the treatment of disorders involving $PLA_2$, and in particular the treatment of generalised or localised chronic osteopoenic inflammations, such as rheumatoid polyarthritis or parodontitis, respectively.

The present invention relates also to the use of compounds of formula (I'):

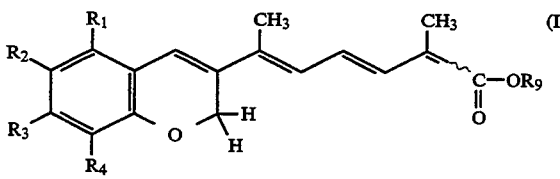

in which:
$R_1$, $R_2$, $R_3$ and $R_4$, which are the same or different, are selected from:
hydrogen,
halogen,
R', and
OR',
R' being linear or branched alkyl containing 1 to 6 carbon atoms inclusive that is optionally substituted by one or more hydroxy and/or by one or more halogens, $R_9$ is selected from hydrogen, linear or branched alkyl containing 1 to 6 carbon atoms inclusive, and a residue of an amino-sugar, for example glucuronide, the non-defined bond carrying the radical $$-\underset{\underset{O}{\|}}{C}-OR_9$$

being a single bond conferring a Z- or E-configuration on the double bond supporting it, and, where applicable, their stereoisomers and addition salts with a pharmaceutically-acceptable acid or base (compounds described in Patent Application EP-A-337885), for the preparation of pharmaceutical compositions for use in the treatment of osteoporosis and of inflammatory disorders, and more especially in generalised or localised chronic osteopoenic inflammations, such as rheumatoid polyarthritis or parodontitis, respectively.

The invention relates also to pharmaceutical compositions containing as active ingredient at least one compound of the general formula (I) or (I') or an addition salt thereof with a pharmaceutically-acceptable acid or base, on its own or in combination with one or more suitable inert, non-toxic excipients.

The pharmaceutical compositions so obtained will be in various forms, the most advantageous being gelatin capsules, suppositories, injectable or drinkable solutions, patches, tablets, dragées, sublingual tablets, sachets, paquets, glossettes, lozenges, creams, ointments, dermic gels and aerosols.

The dosage used may be adapted according to the nature and severity of the disorder, the mode of administration and the age and weight of the patient. In general, the unit dose will range from 10 mg to 200 mg per day in one or two doses.

The following Examples illustrate the invention without limiting it in any way. The starting materials are known or are prepared by known methods.

EXAMPLE 1: (2E, 4E, 6E) -7-(6,8-Dimethyl-2H-chromen-3-yl) hepta-2,4,6-trienoic acid Step A: 3,5-Dimethylsalicylaldehyde A mixture of 30.5 g (250 mmol) of 2,4-dimethylphenol, 18.9 g (135 mmol) of hexamethylenetetramine and 18.9 g (210 mmol) of paraformaldehyde is heated to 100° C., with stirring. 75 ml of acetic acid are then added dropwise. The whole is brought to 110° C. over a period of 15 minutes, with stirring. 17 ml of sulphuric acid and 6 ml of water are added dropwise over a period of 15 minutes. Stirring is continued at 110° C. for 30 minutes, and then the mixture is poured into 500 ml of hot water. The whole is extracted 3 times with methylene chloride, and then the combined organic phases are washed until neutral with an aqueous sodium hydrogen carbonate solution. Drying over sodium sulphate, evaporation and removal of the solvent by distillation yield 30.04 g of a yellow oil.

Yield: 80% IR spectrum: (KBr) $\nu$ OH=3200 to 2800 cm$^{-1}$ $\nu$ CH3=2970 cm$^{-1}$; 2910 cm$^{-1}$ $\nu$ OC=O=1655 cm$^{-1}$

Step B: (6,8-Dimethyl-2H-chromen-3-yl)carboxaldehyde 7.9 g (52.6 mmol) of the compound obtained in Step A and 4.66 g (83.22 mmol) of acrolein are added, at room temperature, to a solution of 11.48 g (83.22 mmol) of potassium carbonate in 120 ml of anhydrous dioxane. The mixture is refluxed for 2 hours, with stirring. The reaction mixture is evaporated on a water bath, in vacuo, and the residue is taken up in 200 ml of water and extracted 3 times with 100 ml of diethyl ether. The combined organic phases are washed until neutral with a saturated aqueous sodium chloride solution and are then dried over sodium sulphate. Filtration, concentration and purification of the oily residue over silica gel (eluant: methylene chloride/petroleum ether, 50:50) yield 7.82 g of product.

Yield: 52% Melting point: 52°-54° C.

Step C: (E)-2-(6,8-Dimethyl-2H-chromen-3-yl)-1-(1,3-dioxolan-2-yl)ethene 6.67 g (18.7 mmol) of tributyl-(1,3-dioxolan-2-yl)methylphosphonium bromide (obtained by reaction of tributylphosphine with 2-bromoethyl-1,3-dioxolane) and 3.52 g (18.7 mmol) of the compound obtained in Step B are mixed with 120 ml of anhydrous dimethylformamide. The whole is heated to 90° C., and then 1.27 g (18.7 mmol) of sodium ethoxide (1M solution in absolute ethanol) are added dropwise under a nitrogen atmosphere. After 16 hours at 90° C., the dimethylformamide is evaporated off under reduced pressure and the reaction mixture is taken up in 150 ml of water. After customary treatment of the organic phase, the residue is purified by elution with methylene chloride over silica gel, yielding, after evaporation of the solvent, 2.66 g of the desired acetal.

Yield: 55% Melting point: 62°-64° C.

Step D: (2E)-3-(6,8-Dimethyl-2H-chromen-3-yl)propenal 2.6 g (10.05 mmol) of the acetal obtained in Step C are dissolved in 80 ml of tetrahydrofuran, to which 80 ml of a 2.5M aqueous hydrochloric acid solution are added.

The reaction proceeds for 2 hours at room temperature, and then the reaction mixture is hydrolysed with 250 ml of water. Taking up the product in diethyl ether, customary treatment of the organic phase and purification by chromatography over a silica column (eluant: petroleum ether/methylene chloride, 50:50) yield 2.15 g of yellow crystals recrystallised from petroleum ether.

Yield: 85% Melting point: 76°-78° C.

Step E: (2E,4E)-5-(6,8-Dimethyl-2H-chromen-3-yl)-penta-2,4-dienal 3.31 g (15.47 mmol) of the propenal obtained in Step D are again subjected to the Wittig reaction described in Step C; the acetal so obtained is hydrolysed by the method described in Step D, yielding 2.53 g of orange crystals recrystallised from diisopropyl ether.

Yield: 68% Melting point: 109°-111° C.

Step F: Ethyl (2E,4E,6E)-7-(6,8-Dimethyl-2H-chromen-3-yl)hepta-2,4,6-trienoate 0.43 ml (2.16 mmol) of ethyl diethylphosphonoacetate is added dropwise to a mixture of 0.083 g (2.16 mmol) of sodium hydride and 80 ml of anhydrous benzene cooled to −5° C. The whole is left to stand for 45 minutes until it has returned to room temperature, and then it is again cooled to −5° C. A solution of 0.52 g (2.16 mmol) of chromenylpentadienal obtained in Step E in benzene is then added dropwise; after 4 hours at room temperature, the solvent is evaporated off in vacuo, and the reaction mixture is taken up in 150 ml of water and then in methylene chloride. Customary treatment of the organic phase and purification over a silica column (eluant: methylene chloride/petroleum ether, 75:25) yield 0.54 g of a yellow powder, corresponding to the E isomer.

Yield: 70% Melting point: 108°-110° C.

Step G: (2E,4E,6E)-7-(6,8-Dimethyl-2H-chromen-3-yl)hepta-2,4,6-trienoic acid 0.561 g (1.41 mmol) of the ester obtained in Step F and 1.15 ml (5.66 mmol) of a 5N aqueous sodium hydroxide solution are heated at 90° C. over a period of 4 hours in 80 ml of ethanol. After evaporating off the solvent and taking up the reaction mixture in 40 ml of water, the reaction mixture is acidified with a 1N hydrochloric acid solution. The resulting precipitate is filtered, washed and recrystallised from ethanol, yielding 0.34 g of a yellow powder.

Yield: 85% Melting point: 208°-210° C.

EXAMPLE 2: (2Z,4E,6E)-7-(6,8-Dimethyl-2H-chromen-3-yl)hepta-2,4,6-trienoic acid Compound obtained according to the same scheme as in Example 1 by isolating the 2Z isomer in the purification described in Step F.

The following compounds are obtained analogously to example 1.

EXAMPLE 3: (2E,4E,6E)-7-(2H-Chromen-3-yl)hepta-2,4,6-trienoic acid

Melting point: 206°-208° C. (yellow crystals, solvent: THF)

EXAMPLE 4: (2E,4E,6E)-7-(6-Methyl-2H-chromen-3-yl)hepta-2,4,6-trienoic acid

Melting point: 235°-240° C. (yellow crystals, solvent: THF/petroleum ether, 80:20)

EXAMPLE 5: (2E,4E,6E)-7-(6-Isopropyl-2H-chromen-3-yl)hepta-2,4,6-trienoic acid Melting point: 244°-246° C. (yellow crystals, solvent: THF)

EXAMPLE 6: (2E,4E,6E)-7-(6-Tert.-butyl-2H-chromen-3-yl)hepta-2,4,6-trienoic acid Melting point: 200°-202° C. (orange crystals, solvent: THF)

EXAMPLE 7:
(2E,4E,6E)-7-(6-Trifluoromethyl-2H-chromen-3-yl)hepta-2,4,6-trienoic acid Melting point: 208°–210° C. (orange crystals, solvent: THF/water, 80:20)

EXAMPLE 8:
(2E,4E,6E)-7-(6-Methoxy-2H-chromen-3-yl)hepta-2,4,6-trienoic acid Melting point: 250°–252° C. (yellow crystals, solvent: THF)

EXAMPLE 9:
(2E,4E,6E)-7-(7-Methoxy-2H-chromen-3-yl)hepta-2,4,6-trienoic acid Melting point: 238°–240° C. (yellow crystals, solvent: THF)

EXAMPLE 10:
(2E,4E,6E)-7-(8-Methoxy-2H-chromen-3-yl)hepta-2,4,6-trienoic acid Melting point: 226°–228° C. (yellow crystals, solvent: THF)

EXAMPLE 11:
(2E,4E,6E)-7-(6-Methyl-8-tert.-butyl-2H-chromen-3-yl)hepta-2,4,6-trienoic acid Melting point: 256°–258° C. (yellow crystals, solvent: THF/ethanol, 80:20)

EXAMPLE 12:
(2E,4E,6E)-7-(6-Tert.-butyl-8-methyl-2H-chromen-3-yl)hepta-2,4,6-trienoic acid Melting point: 225°–227° C. (yellow crystals, solvent: THF/ethanol, 80:20)

EXAMPLE 13:
(2E,4E,6E)-7-(6,8-Ditert.-butyl-2H-chromen-3-yl)hepta-2,4,6-trienoic acid Melting point: 166°–168° C. (yellow crystals, solvent: THF)

EXAMPLE 14:
(2E,4E,6E)-7-(6-Methyl-8-chloro-2H-chromen-3-yl)hepta-2,4,6-trienoic acid Melting point: 248°–250° C. (orange crystals, solvent: THF/water, 80:20)

EXAMPLE 15:
(2E,4E,6E)-7-(6-Chloro-8-methyl-2H-chromen-3-yl)hepta-2,4,6-trienoic acid Melting point: 208°–210° C. (orange crystals, solvent: THF/water, 80:20)

EXAMPLE 16:
(2E,4E,6E)-7-(2,2-Dimethyl-2H-chromen-3-yl)hepta-2,4,6-trienoic acid Melting point: 180°–182° C. (orange crystals, solvent: THF)

EXAMPLE 17:
(2E,4E,6E)-7-(2,2-Dimethyl-6-methoxy-2H-chromen-3-yl)hepta-2,4,6-trienoic acid Melting point: 154°–156° C. (orange crystals, solvent: THF/water, 80:20)

EXAMPLE 18:
(2E,4E,6E)-7-(2,2,6,8-Tetramethyl-2H-chromen-3-yl)hepta-2,4,6-trienoic acid Melting point: 200°–202° C. (yellow crystals, solvent: THF/water, 80:20)

EXAMPLE 19:
(2E,4E,6E)-7-(2,2,8-Trimethyl-6-chloro-2H-chromen-3-yl)hepta-2,4,6-trienoic acid Melting point: 190°–192° C. (yellow crystals, solvent: THF)

EXAMPLE 20:
(2E,4E,6E)-7-(6,8-Dichloro-2H-chromen-3-yl)hepta-2,4,6-trienoic acid Melting point: 280° C. (orange crystals, solvent: THF/petroleum ether, 80:20)

EXAMPLE 21:
(2E,4E,6E)-7-(6-Phenyl-2H-chromen-3-yl)hepta-2,4,6-trienoic acid Step A: 5-Bromo-2-hydroxybenzaldehyde Compound prepared in an identical manner to the compound described in Example 1, Step A.

Step B: 5-Phenyl-2-hydroxybenzaldehyde 0.97 g (1.28 mmol) of trans-benzyl(chloro)bis(triphenylphosphine)palladium(II) is added in a single batch to a solution of 19.7 g (98 mmol) of 5-bromo-2-hydroxybenzaldehyde obtained in Step A and 64 g (149 mmol) of tetraphenyltin in 220 ml of toluene dried over a 4 Å molecular sieve. The mixture is refluxed for 24 hours. After returning to room temperature, the solution is filtered over Celite. 20 ml of a 20% solution of potassium fluoride in methanol are added to the filtrate. After 5 minutes' stirring and filtration, the filtrate is concentrated under reduced pressure. The solid is taken up in 60 ml of methylene chloride and the solution is again filtered. The organic phase is washed with 20 ml of water, recovered and then dried over magnesium sulphate. After removal of the solvent by distillation and filtration, the residual solid is again subjected, twice consecutively, to the same treatment.

Step C: (2E, 4E, 6E)-7-(6-Phenyl-2H-chromen-3-yl)hepta-2,4,6-trienoic acid

The 5-phenyl-2-hydroxybenzaldehyde obtained in Step B is subjected, in an analogous manner, to the treatment described in Example 1, Steps B to G, to give the desired acid.

Melting point: 260° C. (crystallisation solvent: THF/water, 90:10)

EXAMPLE 22: Diethyl (1E,3E,5E)-[6-(6-bromo-2H-chromen-3-yl)hexa-1,3,5-triene]-1-phosphonate Step A: (2E,4E)-5-(6-Bromo-2H-chromen-3-yl)penta-2,4-dienal The 5-bromo-2-hydroxybenzaldehyde obtained in Example 21, Step A, is subjected to the treatment described in Example 1, Steps B to E.

Step B: Diethyl (1E, 3E, 5E)-[6-(6-Bromo-2H-chromen-3-yl)-hexa-1,3,5-triene]-1-phosphonate The synthesis in this step is analogous to that in Example 1, Step F, using diethyl diethylphosphonomethylenephosphonate in place of ethyldiethylphosphonoacetate.

EXAMPLE 23: Diethyl (1E,3E,5E)-[6-(6-Adamantanyl-2H-chromen-3-yl)hexa-1,3,5-triene]-1-phosphonate Compound obtained in a similar manner to that obtained in Example 21, Steps A and B, then Example 22, Step B.

EXAMPLE 24: Ethyl (2E, 4E, 6E)-7-(6,8-Di-adamantanyl-2H-chromen-3-yl)hepta-2,4,6-trienoate Step A: 5,7-Di-adamantanyl-2-hydroxybenzaldehyde Intermediate prepared analogously to that described in Example 21, Steps A and B.

Step B: Ethyl (2E,4E,6E)-7-(6,8-di-adamantanyl-2H-chromen-3-yl)hepta-2,4,6-trienoate The 5,7-di-adamantanyl-2-hydroxybenzaldehyde obtained in Step A is subjected, in an analogous manner, to the treatment described in Example 1, Steps B to F, to give the desired product.

EXAMPLE 25: Ethyl (2E,4E,6E)-3-methyl-7-(6-phenyl-2-H-chromen-3-yl)octa-2,4,6-trienoate Step A: 3-Acetyl-6-bromo-2H-chromene A heterogeneous solution of 100 g (497 mmol) of 5-bromo-2-hydroxybenzaldehyde and 13.8 g (10 mmol) of potassium carbonate (previously finely ground and dried at 90° C.) in 220 ml of butan-2-one is brought to reflux. A solution of 35.31 g (i.e. 42 ml, 497 mmol) of but-3-en-2-one in 40 ml of butan-2-one is then added dropwise over a period of from 15 to 20 minutes. After 4 hours' refluxing, 13.8 g (10 mmol) of potassium carbonate are added. The mixture is refluxed for 16 hours. When the reaction mixture has returned to room temperature, the solid is separated off by filtration and then washed with 2×50 ml of butan-2-one. The filtrate is then concentrated and the residue is purified by chromatography over a silica column (eluant: methylene chloride/cyclohexane, 1:1). Recrystallisation from diisopropyl ether yields 73 g of a yellowish solid.

Yield: 58% Melting point: 70° C.

Step B: 3-Acetyl-6-phenyl-2H-chromene 0.97 g (1.28 mmol) of trans-benzyl(chloro)bis(triphenylphosphine)palladium(II) is added in a single batch to a solution of 25 g (98 mmol) of 3-acetyl-6-bromo-2H-chromene obtained in Step A and 64 g (149 mmol) of tetraphenyltin in 220 ml of toluene dried over a 4 Å molecular sieve. The mixture is refluxed for 24 hours. After returning to room temperature, the solution is filtered over Celite. 20 ml of a 20% solution of potassium fluoride in methanol are added to the filtrate. After 5 minutes' stirring and filtration, the filtrate is concentrated under reduced pressure. The solid is taken up in 60 ml of methylene chloride and the solution is again filtered. The organic phase is washed with 20 ml of water, recovered and then dried over magnesium sulphate.

After removal of the solvent by distillation and filtration, the residual solid is again subjected, twice consecutively, to the same treatment. 12 g of a yellow solid are obtained.

Yield: 42% Melting point: 126° C.

Step C: Ethyl 3-hydroxy-3-(6-phenyl-2H-chromen-3-yl)butanoate 4.35 g (0.0665 At-g) of activated zinc are covered with 12 ml of dimethoxymethane, and then 1 ml (9 mmol) of pure ethyl bromoacetate is added under an argon atmosphere. After induction of the reaction by heating, a solution of 6.38 ml (57.5 mmol) of ethyl bromoacetate in 20 ml of dimethoxymethane is added in such a manner as to maintain reflux. After the zinc has been completely consumed and the reaction mixture has returned to room temperature, a solution of 11.1 g (43.5 mmol) of 3-acetyl-6-phenyl-2H-chromene in 60 ml of anhydrous tetrahydrofuran is added dropwise over a period of from 10 to 15 minutes. After one hour's stirring at room temperature, the mixture, cooled to +4° C., is treated with 25 ml of a 10% sulphuric acid solution. After addition of 70 ml of diethyl ether, the aqueous phase is separated off, and the ethereal phase is washed with 3×20 ml of water and then dried over magnesium sulphate. The solvents are evaporated off under reduced pressure, yielding a solid which is used in the following step without additional purification.

Step D: Ethyl 3-(6-phenyl-2H-chromen-3-yl)but-2-enoate

The whole of the solid obtained in Step C is dissolved in 70 ml of toluene and then treated with 1.25 ml (13.3 mmol) of phosphorus oxychloride. The mixture is refluxed for one hour. After returning to room temperature, the reaction mixture is poured onto 60 ml of ice-water and then mixed with 100 ml of diethyl ether. Customary treatment of the organic phase yields, after purification over a silica column (eluant: methylene chloride), 12.36 g of a yellow solid recrystallised from diisopropyl ether.

Yield: 87% Melting point: 97° C.

Step E: 3-(6-Phenyl-2H-chromen-3-yl)but-2-en-1-ol 3.47 g (98 mmol) of lithium aluminium hydride are added to a solution, which is kept at 0° C. and under argon, of 4.95 g (37 mmol) of sublimed anhydrous aluminium chloride and 50 ml of diethyl ether. The resulting complex is stirred at 0° C. for 20 minutes, and then a solution of 11.9 g (37.1 mmol) of the ester obtained in Step D in 130 ml of a mixture of diethyl ether and tetrahydrofuran (10:3) is added rapidly. The whole is kept at 0° C. for 45 minutes. The excess hydride is decomposed by the addition, in succession, of 10 ml of 0.4N hydrochloric acid, 10 ml of 1N hydrochloric acid and 20 ml of 4N hydrochloric acid. After dilution with 100 ml of water, the reaction mixture is extracted with diethyl ether (from 500 to 2000 ml). The ethereal phases are treated in the customary manner, yielding a pale yellow liquid which is used directly in the following step without additional purification.

Step F: 3-(6-Phenyl-2H-chromen-3-yl)but-2-enal 29.36 g (33.7 mmol) of manganese dioxide are added in three batches, at 15 minute intervals, to a solution of 9.4 g (33.7 mmol) of the alcohol obtained in Step E in 160 ml of anhydrous methylene chloride. After one hour's stirring, the reaction mixture is filtered over Celite and the methylene chloride is removed by evaporation under reduced pressure. The crude product is crystallised from diisopropyl ether, yielding, finally, 8.27 g of a yellow solid.

Yield: 89% Melting point: 147° C.

Step G: Ethyl (2E,4E,6E)-3-methyl-7-(6-phenyl-2H-chromen-3-yl)octa-2,4,6-trienoate 0.905 g (37.7 mmol) of sodium hydride is added, in small portions, under argon, to a solution of 9.49 g (36 mmol) of ethyl (E)-4-diethoxyphosphoryl-3-methylbut-2-enoate in 70 ml of anhydrous tetrahydrofuran. After 30 minutes' stirring, a solution of 8.27 g (30 mmol) of the aldehyde obtained in Step F in 140 ml of tetrahydrofuran is added dropwise over a period of 30 minutes.

After one hour's stirring, the reaction mixture is cooled to 10° C., and there are added dropwise 100 ml of distilled water, then 45 ml of a 0.1N hydrochloric acid solution, and finally 140 ml of water. After allowing to stand for one hour at +10° C., the yellow solid is separated off by filtration and washed abundantly with water. After drying at 70° C. over phosphoric acid under vacuum, 11.5 g of the trienic ester are recovered in the form of a mixture of (2E,4E,6E) and (2Z,4E,6E) isomers and are then recrystallised twice from diethyl ether and ethanol, yielding, finally, 7.34 g of a yellow solid.

Yield: 63% Melting point: 159° C.

EXAMPLE 26: (2E,4E,6E)-3-Methyl-7-(6-phenyl-2H-chromen-3-yl)octa-2,4,6-trienoic acid 44 ml of 35% sodium hydroxide are added to a solution of 7.34 g (19 mmol) of the ester obtained in Example 25 in a mixture of 310 ml of ethanol and 140 ml of distilled water. The reaction mixture is then refluxed for 2 hours. The solution, cooled to +10° C., is acidified to pH 4 by means of a 4N hydrochloric acid solution. After the addition of 80 ml of water, the mixture is stirred at +10° C. for one hour. After filtration, the solid is rinsed with water and dried in a vacuum oven at 70° C. over phosphoric acid. Recrystallisation from ethanol yields 4.6 g of a yellow solid.

Yield: 67% Melting point: 249° C. (decomposition)

EXAMPLE 27: Ethyl (2Z,4E,6E)-3-methyl-7-(6-phenyl-2H-chromen-3-]yl-)octa-2,4,6-trienoate The mother liquors from crystallisation of the compound described in Example 25, Step G, are evaporated under reduced pressure, and the solid so obtained is chromatographed over a silica column (eluant: methylene chloride), yielding 2.8 g of a yellow solid.

Yield: 24.3% Melting point: 159° C. (recrystallised from ethanol)

EXAMPLE 28: (2Z,4E,6E)-7-(6-Phenyl-2H-chromen-3-yl)-3-methylocta-2,4,6-trienoic acid The protocol described in Example 26 is applied to the compound obtained in Example 27.

Yield: 78% Melting point: >250° C. (decomposition)

The following esters were obtained analogously to the process described in Example 1.

EXAMPLE 29: Ethyl (2E,4E,6E)-7-(6-adamantanyl-2H-chromen-3-yl)-3-methylocta-2,4,6-trienoate

EXAMPLE 30: Ethyl (2E,4E,6E)-7-[6-(2-pyridyl)-2H-chromen-3-yl]-3-methylocta-2,4,6-trienoate

EXAMPLE 31: Ethyl (2E,4E,6E)-7-[6-(2-thienyl)-2H-chromen-3-yl]-3-methylocta-2,4,6-trienoate The following esters were obtained analogously to the process described in Example 25, omitting Step B, from the appropriate hydroxybenzaldehydes.

EXAMPLE 32: Ethyl (2E,4E,6E)-7-(6-methyl-2H-chromen-3-yl)-3-methylocta-2,4,6-trienoate Melting point: 135° C. (crystallisation solvent: ethanol)

EXAMPLE 33: Ethyl (2E,4E,6E)-7-(6-tert.-butyl-2H-chromen-3-yl)-3-methylocta-2,4,6-trienoate Melting point: 129° C. (crystallisation solvent: ethanol)

EXAMPLE 34: Ethyl (2E,4E,6E)-7-(6-trifluoromethyl-2H-chromen-3-yl)-3-methylocta-2,4,6-trienoate Melting point: 163°–165° C. (crystallisation solvent: ethanol)

EXAMPLE 35: Ethyl (2E,4E,6E)-7-(6,8-dimethyl-2H-chromen-3-yl)-3-methylocta-2,4,6-trienoate Melting point: 122° C. (crystallisation solvent: diisopropyl ether)

EXAMPLE 36: Ethyl (2E,4E,6E)-7-(6-tert.-butyl-8-methyl-2H-chromen-3-yl)-3-methylocta-2,4,6-trienoate Melting point: 73° C. (crystallisation solvent: heptane)

EXAMPLE 37: Ethyl (2E,4E,6E)-7-(6,8-ditert.-butyl-2H-chromen-3-yl)-3-methylocta-2,4,6-trienoate Melting point: 130°–131° C. (crystallisation solvent: diisopropyl ether)

EXAMPLE 38: Ethyl (2E,4E,6E)-7-(7-methoxy-2H-chromen-3-yl)-3-methylocta-2,4,6-trienoate

EXAMPLE 39: Ethyl (2E,4E,6E)-7-(2,2-dimethyl-6-ethyl-2H-chromen-3-yl)-3-methylocta-2,4,6-trienoate The following acids were prepared analogously to the compound described in Example 26 from their respective esters:

EXAMPLE 40: (2E,4E,6E)-7-(6-Methyl-2H-chromen-3-yl)-3-methylocta-2,4,6-trienoic acid Melting point: 244° C. (decomposition) (crystallisation solvent: ethanol)

EXAMPLE 41:
(2E,4E,6E)-7-(6-Tert.-butyl-2H-chromen-3-yl)-3-methylocta-2,4,6-trienoic acid Melting point: 229°–231° C. (decomposition) (crystallisation solvent: ethyl acetate)

EXAMPLE 42:
(2E,4E,6E)-7-(6-Trifluoromethyl-2H-chromen-3-yl)-3-methylocta-2,4,6-trienoic acid Melting point: 245°–246° C. (crystallisation solvent: ethanol/ethyl acetate)

EXAMPLE 43:
(2E,4E,6E)-7-(6,8-Dimethyl-2H-chromen-3-yl)-3-methylocta-2,4,6-trienoic acid Melting point: 233°–235° C. (decomposition) (crystallisation solvent: ethyl acetate)

EXAMPLE 44:
(2E,4E,6E)-7-(6-Tert.-butyl-8-methyl-2H-chromen-3-yl)-3-methylocta-2,4,6-trienoic acid Melting point: 227°–228° C. (crystallisation solvent: ethyl acetate)

EXAMPLE 45:
(2E,4E,6E)-7-(6,8-Ditert.-butyl-2H-chromen-3-yl)-3-methylocta-2,4,6-trienoic acid Melting point: 240°–241° C. (crystallisation solvent: ethanol)

The following two Examples are carried out according to the same method as Example 25, the Horner reagent in this case being diethyl-(3-diethoxyphosphoryl-2-methylprop-1-ene)-1-phosphonate:

EXAMPLE 46: Diethyl (1E, 3E, 5E)-[2-methyl-6-(6,8-dimethyl-2H-chromen-3-yl)hepta-1,3,5-triene]-1-phosphonate Melting point: 95°–96° C. (crystallisation solvent: petroleum ether)

EXAMPLE 47: Diethyl (1E,3E,5E)-[2-methyl-6-(6-methyl-8-tert.-butyl-2H-chromen-3-yl)hepta-1,3,5-triene]-1-phosphonate

EXAMPLE 48:
(1E,3E,5E)-[2-Methyl-6-(2,2-dimethyl-7-methoxy-2H-chromen-3-yl) hepta-1,3,5-triene]-1-phosphonic acid Compound prepared according to the protocol described in Example 26 from the corresponding diethyl phosphonate.

EXAMPLE 49:
(2Z,4E,6E)-3-Methyl-7-(6-adamantan-1-yl-2H-chromen-3-yl)octa-2,4,6-trienoic acid Compound obtained from the ester described in Example 29, according to the process of Example 26.
Melting point: 247° C. (decomposition)

EXAMPLE 50: Ethyl (2E,4E,6E)-3-methyl-7-(6-adamantan-1-yl-2H-chromen-3-yl)octa-2,4,6-trienoate The title product is isolated by the procedure described in Example 27, using the mother liquors obtained in Example 29.
Melting point: 178°–179° C.

EXAMPLE 51:
(2E,4E,6E)-3-Methyl-7-(6-adamantan-1-yl-2H-chromen-3-yl)octa-2,4,6-trienoic acid The compound obtained in Example 50 is hydrolysed according to the method described for Example 26.
Melting point: >250° C.

PHARMACOLOGICAL STUDY

Example A: Anti-bone resorption-1

Anti-bone resorption properties have been demonstrated on mouse calvaria according to a model inspired by the method described by Reynolds and Dingle ("A sensitive in vitro method for studying the induction and inhibition of bone resorption", *Calc. Tiss. Res.*, (1970), 339–349. The compounds were studied on a tissue in hyperresorption, which had been induced by the addition of $5 \times 10^{-8}$M of retinoic acid. The results obtained are given in Table I below:

TABLE I

| | Anti-bone resorption | |
|---|---|---|
| Example | Concentration (μM) | Inhibition of resorption (%) |
| 25 | 50 | 15 |
| 26 | 10 | 11 |
|    | 50 | 29 |
| 27 | 10 | 11 |
| 32 | 10 | 14 |
|    | 50 | 12 |
| 33 | 10 | 3 |
| 35 | 10 | 15 |
|    | 50 | 32 |
| Reference: Etretinate | 50 | 11 |

This activity manifests itself in a comparable manner when hyper-resorption is induced by the addition of parathormone (PTH) (500 ng/ml).

| Example | Hyper-resorption with retinoic acid | Hyper-resorption with PTH |
|---|---|---|
| 35 (7,5 μM) | 9% | 12% |

Example B: Anti-bone resorption-2

In vivo study according to the measurement method described by Konig, Muhlbauer and Fleisch ("Tumor necrosis factor and interleukine-1 stimulate bone resorption in vivo as measured by urinary [$^3$H] tetracycline excretion from prelabeled mice", *J. Bone Min. Res.*, 3, (1988), 621–627). A study was carried out on mice in which a state of hyper-resorption had been induced by a calcium-deficient diet (0.4%). Hyper-resorption was seen to cease after treatment with one of the compounds of the invention, unlike etretinate, which tends to increase the urinary excretion of tritiated tetracycline. The results are given in Table II below:

TABLE II

| | % variation in urinary [$^3$H] tetracycline excretion | | |
|---|---|---|---|
| | Oral dose (mg/kg) | | |
| | 50 | 100 | 200 |
| Example 2 | −10% | −10% | −12 |
| Etretinate | +11% | +3% | — |

Example C: Formation of osteoid tissue

An effect promoting the formation of osteoid tissue (incorporation of tritiated proline from the medium into the bone tissue of mouse calvaria) has also been observed with some compounds:

| Exmple | Concentration (μM) | Stimulation of formation |
|---|---|---|
| 26 | 10 | +7% |
| 35 | 10 | +11% |

Example D: Anti-inflammatory activity

The compounds of the present invention have an inhibiting activity on the liberation of tritiated oleic acid previously incorporated into *Escherichia coli* membranes under the effect of porcine pancreatic phospholipase $A_2$ (PLA$_2$) according to the technique described by Frason, Patriarca and Elsbach (*J. Lipid. Res.*, 15, (1974), 380–388). The results are shown in Table III below:

TABLE III

| Test on *Escherichia coli* membranes | | | |
|---|---|---|---|
| Example | IC$_{50}$ (μM) | Example | IC$_{50}$ (μM) |
| 5 | 7,5 | 20 | 8 |
| 6 | 9 | 25 | 5 |
| 11 | 6 | 26 | 5 |
| 13 | 3 | 27 | 7,5 |
| 14 | 20 | 32 | 7,5 |
| 15 | 10 | 35 | 5 |
| 18 | 30 | 36 | 5 |
| 19 | 30 | 41 | 4 |

Example E: Test on rat polymorphonuclears

In a cell model involving endogenous membrane PLA$_2$, the compounds of the invention also exerted an inhibiting effect on the liberation of arachidonic acid by their action on isolated rat polymorphonuclears (PLN), the membrane phospholipids of which had been labelled with tritiated arachidonic acid. The degree of activity of the compounds of the invention is assessed by measuring the radioactivity liberated after stimulation by ionophore A 12187 according to the technique described by Sakson, Raz, Denny, Wyche and Needleman (*Prostaglandins*, 14, (1977), 853, sqq.).

The results are shown in Table IV below:

TABLE IV

| Test on rat PMNs | |
|---|---|
| Example | IC$_{50}$ (μM) |
| 5 | 30 |
| 6 | 10 |
| 11 | 5 |
| 13 | 5 |
| 14 | 50 |
| 15 | 50 |
| 18 | 30 |
| 19 | 50 |
| 20 | 30 |

We claim:

1. A compound selected from those of formula (I):

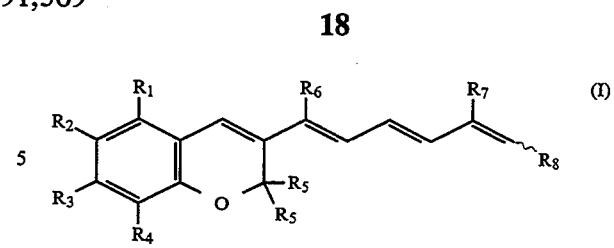

in which:

$R_1$, $R_2$, $R_3$ and $R_4$, which are the same or different, represent:
hydrogen,
halogen,
phenyl,
adamantyl,
a heterocycle, selected from furyl, pyrrolyl, pyrrolidinyl, thienyl, pyridyl, piperidyl, indolyl and quinolyl,
R', or
OR',
R' being linear or branched alkyl having 1 to 6 carbon atoms inclusive which is optionally substituted by one or more hydroxy and/or by one or more halogens, $R_5$, $R_6$ and $R_7$, which are the same or different, are selected from hydrogen and linear or branched alkyl having 1 to 6 carbon atoms inclusive, $R_8$ is selected from C(O)OR$_9$, P(O)(OR$_9$)$_2$ and CONHR$_{10}$ in which R$_9$ is hydrogen or linear or branched alkyl containing 1 to 6 carbon atoms inclusive, and R$_{10}$ represents hydrogen, linear or branched alkyl having 1 to 6 carbon atoms inclusive, or carbocyclic aryl, the non-defined bond carrying R$_8$ being a single bond conferring an E- or Z-configuration on the double bond supporting it, with the proviso that when one or both R$_5$ represent hydrogen hydrogen and R$_6$ and R$_7$ each represents hydrogen at lower alkyl and R$_8$ represents C(O)OR$_9$ as defined above, then at least one of the substituents $R_1$, $R_2$, $R_3$ and $R_4$ is other than hydrogen, halogen, R' and OR', R' being as defined above, its stereoisomers and, where appropriate, its addition salts with a pharmaceutically-acceptable acid or base.

2. A compound according to claim 1 which is selected (2E,4E,6E)-3-methyl-7-(6-phenyl-2H-chromen-3-yl)octa-2,4,6-trienoic acid, and its addition salts with a pharmaceutically-acceptable base.

3. A compound according to claim 1 which is ethyl (2Z,4E,6E)-3-methyl-7-(6-phenyl-2H-chromen-3-yl)octa-2,4,6-trienoate.

4. A compound according to claim 1 which is diethyl (1E,3E,5E)-[2-methyl-6-(6,8-dimethyl-2H-chromen-3-yl)hepta-1,3,5-triene]-1-phosphonate.

5. A compound according to claim 1 which is selected from (2E,4E,6E)-7-(6-Phenyl-2H-chromen-3-yl)hepta-2,4,6-trienoic acid, and its addition salts with a pharmaceutically-acceptable base.

6. A compound according to claim 1 which is selected from Diethyl (1E,3E,5E)-[6-(6-Adamantyl-2H-chromen-3-yl)hexa-1,3,5triene]-1-phosphonate, and its addition salts with a pharmaceutically-acceptable base.

7. A compound according to claim 1 which is selected from Ethyl (2E,4E,6E)-7-(6,8-Di-adamantanyl-2H-chromen-3-yl)hepta-2,4,6-trienoate, and its addition salts with a pharmaceutically-acceptable base.

8. A compound according to claim 1 which is selected from Ethyl (2Z,4E,6E)-3-methyl-7-(6-phenyl-2H-chromen-3-yl)octa-2,4,6-trienoate, and its addition salts with a pharmaceutically-acceptable base.

9. A pharmaceutical composition useful as an antiosteoporotic agent which contains as active ingredient an effective amount of a compound according to claim 1, in combination with one or more pharmaceutically-acceptable, inert excipients or vehicles.

10. A method of treating a mammal afflicted with a disease requiring an antiosteoporotic agent, resulting from osteoporosis, or an inflammatory disorder, comprising the step of administering to the said mammal an amount of a compound selected from those of formula (I):

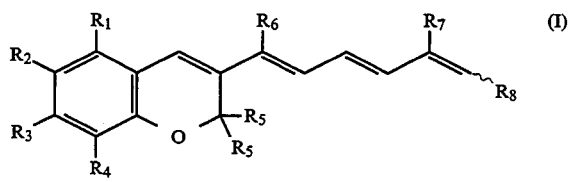

in which:
$R_1$, $R_2$, $R_3$ and $R_4$, which are the same or different, are selected from:
hydrogen,
halogen,
phenyl,
adamantyl,
a heterocycle selected from furyl, pyrrolyl, pyrrolidinyl, thienyl, pyridyl, piperidyl, indolyl and quinolyl,
R', and
OR',
R' being linear or branched alkyl having 1 to 6 carbon atoms inclusive which is optionally substituted by one or more hydroxy and/or by one or more halogen atoms,
$R_5$, $R_6$ and $R_7$, which are the same or different, are selected from hydrogen and linear or branched alkyl having 1 to 6 carbon atoms inclusive,
$R_8$ is selected from $C(O)OR_9$, $P(O)(OR_9)_2$ and $CONHR_{10}$ in which $R_9$ is selected from hydrogen and linear or branched alkyl having 1 to 6 carbon atoms inclusive, and $R_{10}$ represents hydrogen, linear or branched alkyl having 1 to 6 carbon atoms inclusive, or carbocyclic aryl,
the non-defined bond carrying $R_8$ being a single bond conferring an E- or Z-configuration on the double bond supporting it, and, where applicable, a stereoisomer and an addition salt thereof with a pharmaceutically-acceptable acid or base, for alleviation of said disease.

11. A method of claim 10, wherein the compound is selected from (2E,4E,6E)-7-(2,2-dimethyl-6-methoxy-2H-chromen-3-yl)hepta-2,4,6-trienoic acid and its addition salts with a pharmaceutically-acceptable base.

12. A method of claim 10, wherein the compound is selected from (2E,4E,6E)-7-(6-tert.-butyl-2H-chromen-3-yl)hepta-2,4,6-trienoic acid and its addition salts with a pharmaceutically-acceptable base.

13. A method of claim 10, wherein the compound is selected from (2E,4E,6E)-7-(6,8-ditert.-butyl-2H-chromen-3-yl)hepta-2,4,6-trienoic acid and its addition salts with a pharmaceutically-acceptable base.

14. A method of claim 10, wherein the compound is selected from (2E,4E,6E)-3-methyl-7-(6-phenyl-2H-chromen-3-yl)octa-2,4,6-trienoic acid and its addition salts with a pharmaceutically-acceptable base.

15. A method of claim 10, wherein the compound is ethyl (2Z,4E,6E)-3-methyl-7-(6-phenyl-2H-chromen-3-yl)octa-2,4,6-trienoate.

16. A method of claim 10, wherein the compound is diethyl (1E,3E,5E)-[2-methyl-6-(6,8-dimethyl-2H-chromen-3-yl)hepta-1,3,5-triene]-1-phosphonate.

17. A method of claim 10, wherein the compound is selected from (2E,4E,6E)-7-(6-Phenyl-2H-chromen-3-yl)hepta-2,4,6-trienoic acid and its addition salts with a pharmaceutically-acceptable base.

18. A method of claim 10, wherein the compound is selected from Diethyl (1E,3E,5E)-[6-(6-Adamantyl-2H-chromen-3-yl)hexa-1,3,5-triene]-1-phosphonate and its addition salts with a pharmaceutically-acceptable base.

19. A method of claim 10, wherein the compound is selected from Ethyl (2E,4E,6E)-7-(6,8-Di-adamantanyl-2H-chromen-3-yl)hepta-2,4,6-trienoate and its addition salts with a pharmaceutically-acceptable base.

20. A method of claim 10, wherein the compound is selected from Ethyl (2Z,4E,6E)-3-methyl-7-(6-phenyl-2H-chromen-3-yl)octa-2,4,6-trienoate and its addition salts with a pharmaceutically-acceptable base.

* * * * *

UNITED STATES PATENT AND TRADEMARK OFFICE
CERTIFICATE OF CORRECTION

PATENT NO. : 5,391,569
DATED : February 21, 1995
INVENTOR(S) : Jean-Daniel Brion; Guillaume Le Baut; Guillaume Poissonnet; Lucy De Montarby; Larbi Belachmi; Jacqueline Bonnet; Massimo Sabatini; Charles Tordjman It is certified that error appears in the above-indentified patent and that said Letters Patent is hereby corrected as shown below:

Title Page, Item [56] References Cited, U.S. Patent Documents, line 2, column 3; "Laup" should read -- Lang --

Title Page, Item [56] References Cited, U.S. Patent Documents line 4, column 3; "Chandraratra" should read -- Chandraratna --

Title Page, Item [57], Abstract, line 3 from bottom; "defined the" should read -- defined in the --

Col. 1, line 6; "pounds a" should read -- pounds having a --

Col. 14, line 5; insert -- )- -- at the end of the line.

Col. 14, line 6; delete the ")-" at the beginning of the line

Col. 14, line 56; delete the "(" at the end of the line.

Col. 14, line 57; insert -- ( -- at the beginning of the line

Col. 15, line 37; delete the "(" at the end of the line

Col. 15, line 38; insert -- ( -- at the beginning of the line

Col. 18, line 32; "containing" should read -- having --

UNITED STATES PATENT AND TRADEMARK OFFICE
CERTIFICATE OF CORRECTION

PATENT NO. : 5,391,569
DATED : February 21, 1995
INVENTOR(S) : Jean-Daniel Brion; Guillaume Le Baut; Guillaume Poissonnet; Lucy De Montarby; Larbi Belachmi; Jacqueline Bonnet; Massimo Sabatini; Charles Tordjman It is certified that error appears in the above-indentified patent and that said Letters Patent is hereby corrected as shown below:

Col. 18, line 39; "hydrogen hydrogen" should read -- hydrogen or methyl --

Col. 18, line 40; "at" should read -- or --

Col. 18, line 48; "lected" should read -- lected from --

Col. 18, line 63; "1,3,5triene]" should read -- 1,3,5-triene] --

Signed and Sealed this

Sixth Day of June, 1995

Attest:

BRUCE LEHMAN

*Attesting Officer*       *Commissioner of Patents and Trademarks*